United States Patent [19]

Le

[11] Patent Number: 5,077,445
[45] Date of Patent: Dec. 31, 1991

[54] LIQUID-PHASE ALKYLBENZENE SYNTHESIS USING HYDRATED CATALYST

[75] Inventor: Quang N. Le, Cherry Hill, N.J.

[73] Assignee: Mobil Oil Corp., Fairfax, Va.

[21] Appl. No.: 651,075

[22] Filed: Feb. 6, 1991

[51] Int. Cl.$^5$ .............................................. C07C 2/66
[52] U.S. Cl. ................................... 585/467; 585/446; 585/463; 502/74
[58] Field of Search ........................... 585/467; 502/74

[56] References Cited

U.S. PATENT DOCUMENTS

| | | | |
|---|---|---|---|
| 3,751,504 | 8/1973 | Keown et al. | 260/672 |
| 3,755,483 | 8/1973 | Burress | 260/671 |
| 4,016,218 | 4/1977 | Haag et al. | 260/671 |
| 4,169,111 | 9/1979 | Wight | 585/323 |
| 4,459,426 | 7/1984 | Inwood et al. | 585/323 |
| 4,547,605 | 10/1985 | Kresge et al. | 585/467 |
| 4,954,325 | 9/1990 | Le et al. | 585/467 |
| 4,962,256 | 9/1990 | Rubin et al. | 502/74 |
| 4,992,606 | 2/1991 | Kushnerick et al. | 585/467 |

OTHER PUBLICATIONS

Chu et al., application filed 6/28/90, Ser. No. 545,163.

*Primary Examiner*—Asok Pal
*Assistant Examiner*—P. Achutamurthy
*Attorney, Agent, or Firm*—Alexander J. McKillop; Charles J. Speciale; Edward F. Kenehan, Jr.

[57] ABSTRACT

There is provided a process for the liquid-phase synthesis of an alkylbenzene, such as ethylbenzene, using a particular MCM-22 zeolite catalyst which has been hydrated with liquid water.

13 Claims, No Drawings

LIQUID-PHASE ALKYLBENZENE SYNTHESIS USING HYDRATED CATALYST

CROSS-REFERENCE TO RELATED APPLICATIONS

This application is related to copending U.S. application Ser. No. 469 998 filed Jan. 25 1990, now U.S. Pat. No. 4,992,606, and to copending U.S. application Ser. No. 545,163, filed June 28, 1990. The entire disclosures of these applications are expressly incorporated herein by reference.

BACKGROUND

There is provided a process for the liquid-phase synthesis of an alkylbenzene, such as ethylbenzene, using a particular MCM-22 zeolite catalyst which has been hydrated with liquid water.

Ethylbenzene is a valuable commodity chemical which is currently used on a large scale industrially for the production of styrene monomer. Ethylbenzene may be produced by a number of different chemical processes but one process which has achieved a significant degree of commercial success is the alkylation of benzene with ethylene in the presence of a solid, acidic zeolite catalyst. In the production of ethylbenzene by this process, ethylene is used as the alkylating agent and is reacted with benzene in the presence of the catalyst at temperatures which vary between the critical temperature of benzene up to 900° F. (about 480° C.) at the reactor inlet. The reactor bed temperature may be as much as 150° F. (about 85° C.) above the reactor inlet temperature and typical temperatures for the benzene/ethylene reaction vary from 600° to 900° F. (315° to 480° C.), but are usually maintained above about 700° F. (about 370° C.) in order to keep the content of the more highly alkylated benzenes such as diethylbenzene at an acceptably low level. Pressures typically vary from atmospheric to 3000 psig (about 20785 kPa abs) with a weight ratio of benzene to ethylene from 15:1 to 25:1, usually about 20:1 (benzene:ethylene). Space velocity in the reaction is high, usually in the range of 1 to 6, typically 2 to 5, WHSV based on the ethylene flow, with the benzene space velocity varying accordingly, in proportion to the ratio of the reactants. The products of the reaction include ethylbenzene which is obtained in increasing proportions as temperature increases together with various polyethylbenzenes, principally diethylbenzene (DEB) which also are produced in increasing amounts as reaction temperature increases. Under favorable operating conditions on the industrial scale, an ethylene conversion in excess of 99.8 weight percent may be obtained at the start of the cycle In the commercial operation of this process, the polyalkylated benzenes, including both polymethylated and polyethylated benzenes are recycled to the alkylation reactor in which the alkylation reaction between the benzene and the ethylene takes place. By recycling the by-products to the alkylation reaction, increased conversion is obtained as the polyethylated benzenes (PEB) are converted to ethylbenzene (EB). In addition, the presence of the PEB during the alkylation reaction reduces formation of these species through equilibration of the components because at a given feed composition and under specific operating conditions, the PEB recycle will reach equilibrium at a certain level.

Ethylbenzene production processes are described in U.S. Pat. Nos. 3,751,504 (Keown), 4,547,605 (Kresge) and 4,016,218 (Haag); reference is made to these patents for a detailed description of such processes. The process described in U.S. Pat. No. 3,751,504 is of particular note since it includes a separate transalkylation step in the recycle loop which is effective for converting a significant proportion of the more highly alkylated products to the desired ethylbenzene product Other processes for the production of ethylbenzene are disclosed in U.S. Pat. Nos. 4,169,111 (Wight) and 4,459,426 (Inwood), in both of which a preference for large pore size zeolites such as zeolite Y is expressed, in distinction to the intermediate pore size zeolites used in the processes described in the Keown, Kresge and Haag patents. U.S. Pat. No. 3,755,483 (Burress) describes a process for the production of ethylbenzene using zeolite ZSM-12 as the alkylation catalyst.

The entire disclosures of the above-identified U.S. patents are expressly incorporated herein by reference.

SUMMARY

There is provided a process for preparing an alkylbenzene, said process comprising contacting an olefin having from 2 to 6 carbon atoms and liquid benzene with a catalyst under sufficient alkylation conditions, said catalyst comprising a synthetic porous crystalline material characterized by an X-ray diffraction pattern including values substantially as set forth in Table 1 of the specification, said crystalline material comprising at least 10% by weight of liquid water included in the pore space of the crystalline material when the crystalline material is first contacted with said benzene and olefin, wherein the alkylation conditions include a combination of temperature and pressure sufficient to maintain said benzene and said water in the liquid state. The olefin which is used in this reaction may be an alpha olefin, especially a straight chain alpha olefin, a preferred olefin is ethylene.

EMBODIMENTS

The zeolite, which is included in the catalyst of the present process for preparing an alkylbenzene, is identified in this specification as MCM-22. MCM-22 and the synthesis thereof are described in U.S. Pat. No. 4,954,325, the entire disclosure of which is expressly incorporated herein by reference.

In the aforementioned U.S. application Ser. No. 545,163, filed June 28, 1990, MCM-22 is disclosed as being an excellent and improved catalyst for ethylbenzene manufacture. It has now been discovered that the performance of MCM-22 in this reaction is further enhanced by hydrating the catalyst prior to the reaction. The presence of water inhibits multi-alkylation reactions, thus minimizing the formation of undesirable by-products, especially those having 9 or more carbon atoms. Hydration of the catalyst is maintained during the reaction by running the reaction under liquid-phase conditions at relatively low temperature and moderate pressure.

Hydration of the MCM-22 may occur by placing the MCM-22 in liquid water, e.g., at ambient conditions, for a time sufficient to sorb at least 10% by weight of water in the pore space of the zeolite. In this way, the MCM-22 may become saturated with water.

In the production of an alkylbenzene, benzene is alkylated with an olefin in the presence of a solid, porous acidic catalytic material with a characteristic X-ray diffraction pattern. In its calcined form, the synthetic porous crystalline material component employed in the catalyst is characterized by an X-ray diffraction pattern including the lines shown in Table 1 below:

TABLE 1

| Interplanar d-Spacing (A) | Relative Intensity, $I/I_o \times 100$ |
|---|---|
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

Alternatively, it may be characterized by an X-ray diffraction pattern in its calcined form including the following lines shown in Table 2 below:

TABLE 2

| Interplanar d-Spacing (A) | Relative Intensity, $I/I_o \times 100$ |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

More specifically, the calcined form may be characterized by an X-ray diffraction pattern including the following lines shown in Table 3 below:

TABLE 3

| Interplanar d-Spacing (A) | Relative Intensity, $I/I_o \times 100$ |
|---|---|
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

Most specifically, it may be characterized in its calcined form by an X-ray diffraction pattern including the following lines shown in Table 4 below:

TABLE 4

| Interplanar d-Spacing (A) | Relative Intensity, $I/I_o \times 100$ |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |

TABLE 4-continued

| Interplanar d-Spacing (A) | Relative Intensity, $I/I_o \times 100$ |
|---|---|
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard technique. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 $I/I_o$, where $I_o$ is the intensity of the strongest line or peak, and d (obs.) the interplanar spacing in Angstrom Units (Å), corresponding to the recorded lines, were determined. In Tables 1–4, the relative intensities are given in terms of the symbols W=weak, M=medium, S=strong, VS=very strong. In terms of intensities, these may be generally designated as follows:

| W = | 0–20 |
|---|---|
| M = | 20–40 |
| S = | 40–60 |
| VS = | 60–100 |

These X-ray diffraction patterns are characteristic of all species of the zeolite. The sodium form as well as other cationic forms reveal substantially the same pattern with some minor shifts in interplanar spacing and variation in relative intensity. Other minor variations can occur depending on the ratio of structural components, e.g. silicon to aluminum mole ratio of the particular sample, as well as its degree of thermal treatment.

Zeolite MCM-22 has a chemical composition expressed by the molar relationship:

$$X_2O_3:(n)YO_2,$$

where X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, zeolite MCM-22 has a formula, on an anhydrous basis and in terms of moles of oxides per n moles of $YO_2$, as follows:

$$(0.005-0.1)Na_2O:(1-4)R:X_2O_3:nYO_2$$

where R is an organic component. The Na and R components are associated with the zeolite as a result of their presence during crystallization, and are easily removed by the post-crystallization methods described below.

Zeolite MCM-22 is thermally stable and exhibits a high surface area greater than about 400 m$^2$/gm as measured by the BET (Bruenauer, Emmet and Teller) test and unusually large sorption capacity when compared to previously described crystal structures having similar X-ray diffraction patterns. As is evident from the above formula, MCM-22 is synthesized nearly free of Na cations and thus possesses acid catalysis activity as synthesized. It can, therefore, be used as a component of the alkylation catalyst composition herein without having to first undergo an exchange step. To the extent desired, however, the original sodium cations of the as-synthesized material can be replaced at least in part by established techniques including ion exchange with other cations. Preferred replacement cations include metal ions, hydrogen ions, hydrogen precursor ions, e.g., ammonium and mixtures of such ions.

In its calcined form, zeolite MCM-22 appears to be made up of a single crystal phase with little or no detectable impurity crystal phases and has an X-ray diffraction pattern including the lines listed in above Tables 1-4.

Prior to its use as alkylation catalyst, the zeolite crystals should be subjected to thermal treatment to remove part or all of any organic constituent present in the as-synthesized material.

The zeolite in its as-synthesized form containing organic cations as well as when it is in its ammonium form, can be converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to a limit imposed by the irreversible thermal degradation of the crystalline structure of the zeolite, typically up to about 925° C.

Zeolite MCM-22 can be prepared from a reaction mixture containing sources of alkali or alkaline earth metal (M), e.g., sodium or potassium, cation, an oxide of trivalent element X, e.g., aluminum, an oxide of tetravalent element Y, e.g., silicon, an organic (R) directing agent, described below, and water. The reaction mixture has a composition, in terms of mole ratios of oxides, within the following ranges:

| Reactants | Useful | Preferred |
|---|---|---|
| YO$_2$/X$_2$O$_3$ | 10–60 | 10–40 |
| H$_2$O/YO$_2$ | 5–100 | 10–50 |
| OH$^-$/YO$_2$ | 0.01–1.0 | 0.1–0.5 |
| M/YO$_2$ | 0.01–2.0 | 0.1–1.0 |
| R/YO$_2$ | 0.05–1.0 | 0.1–0.5 |

The organic directing agent for use in synthesizing zeolite MCM-22 from the above reaction mixture is hexamethyleneimine.

In a preferred method of synthesizing zeolite MCM-22, the YO$_2$ reactant contains a substantial amount of solid YO$_2$, e.g., at least about 30 wt. % solid YO$_2$. Where YO$_2$ is silica, the use of a silica source containing at least about 30 wt. % solid silica, e.g., Ultrasil (a precipitated, spray dried silica containing about 90 wt. % silica) or HiSil (a precipitated hydrated SiO$_2$ containing about 87 wt. % silica, about 6 wt. % free H$_2$O and about 4.5 wt. % bound H$_2$O of hydration and having a particle size of about 0.02 micron) favors crystal formation from the above mixture. If another source of oxide of silicon, e.g., Q-Brand (a sodium silicate comprised of about 28.8 wt. % of SiO$_2$, 8.9 wt. % Na$_2$O and 62.3 wt. % H$_2$O) is used, crystallization may yield little if any MCM-22 crystalline material and impurity phases of other crystal structures, e.g., ZSM-12, may be produced. Preferably, therefore, the YO$_2$, e.g., silica, source contains at least about 30 wt. % solid YO$_2$, e.g., silica, and more preferably at least about 40 wt. % solid YO$_2$, e.g., silica.

Crystallization of the MCM-22 crystalline material can be carried out at either static or stirred conditions in a suitable reactor vessel such as, e.g., polypropylene jars or teflon-lined or stainless steel autoclaves. The total useful range of temperatures for crystallization is from about 80° C. to about 225° C. for a time sufficient for crystallization to occur at the temperature used, e.g., from about 25 hours to about 60 days, after which the crystals are separated from the liquid and recovered.

The reaction mixture components can be supplied by more than one source. The reaction mixture can be prepared either batchwise or continuously. Crystal size and crystallization time of the MCM-22 crystalline material will vary with the nature of the reaction mixture employed and the crystallization conditions.

In all cases, synthesis of the MCM-22 crystals is facilitated by the presence of at least about 0.01 percent, preferably about 0.10 percent and still more preferably about 1 percent, seed crystals (based on total weight) of the crystalline product.

The zeolite crystals can be shaped into a wide variety of particle sizes. Generally speaking, the particles can be in the form of a powder, a granule, or a molded product such as an extrudate having a particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

The crystalline material may be composited with another material which is resistant to the temperatures and other conditions employed in the alkylation process of this invention. Such materials include active and inactive materials and synthetic or naturally occurring zeolites as well as inorganic materials such as clays and/or oxides such as alumina, silica or silica-alumina. The latter may be either naturally occurring or in the form of gelatinous precipitates or gels including mixtures of silica and metal oxides Use of a material in conjunction with the zeolite, i.e., combined therewith or present during its synthesis, which itself is catalytically active may change the conversion and/or selectivity of the catalyst. Inactive materials suitably serve as diluents to control the amount of conversion so that alkylation products can be obtained economically and orderly without employing other means for controlling the rate of reaction These materials may be incorporated into naturally occurring clays, e.g., bentonite and kaolin, to improve the crush strength of the catalyst under commercial alkylation operating conditions and function as binders or matrices for the catalyst The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

The stability of the catalyst used in the present process may be increased by steaming U.S. Pat. Nos. 4,663,492; 4,594,146; 4,522,929; and 4,429,176, describe conditions for the steam stabilization of zeolite catalysts which can be utilized to steam-stabilize the catalyst Reference is made to these patents for a detailed description of the steam stabilization technique for use with the present catalysts. The steam stabilization conditions typically include contacting the catalyst with, e.g., 5-100% steam at a temperature of at least about 300° C. (e.g., 300-650° C.) for at least one hour (e.g., 1-200 hours) at a pressure of 101-2,500 kPa. In a more particular embodiment, the catalyst can be made to undergo steaming with 75-100% steam at 315°-500° C. and atmospheric pressure for 2-25 hours. The steaming of the catalyst can take place under conditions sufficient to initially increase the Alpha Value of the catalyst, the significance of which is discussed below, and produce a steamed catalyst having an enhanced Alpha Value. If desired, steaming can be continued to subsequently reduce the Alpha Value from the higher Alpha Value to an Alpha Value which is substantially the same as the Alpha Value of the unsteamed catalyst.

The alkylation reaction is carried out at elevated temperatures in the liquid phase. More particularly, the reaction is carried out with the benzene feedstock in the liquid phase with the reaction conditions (temperature, pressure) appropriate to this end. Suitable conditions can be selected by reference to the phase diagram for benzene. Because the reaction is exothermic, the reactor bed temperature will be higher than the reactor inlet temperatures, typically by as much as about 150° F. (about 85° C.) but generally it is preferred to control the exotherm to a maximum of about 100° F. (55° C.). Liquid phase operation is normally carried out at temperatures between 200° and 500° F. (about 93 to 260° C.), usually in the range of 300 to 500° F. (about 149° to 260° C.).

In a typical low pressure vapor phase operation, the temperature will be from about 600° to 800° F. with the pressure from about 200 to 500 psig. In a typical high pressure liquid phase operation, the temperature will be from about 300° to 600° F. with the pressure in the range of about 400 to 800 psig. The ratio of the benzene to the olefin in the alkylation reactor is typically from 15:1 to 25:1 by weight (benzene olefin) normally about 20:1.

EXAMPLE 1

In this Example and the Example which follows, an MCM-22 catalyst was evaluated in a fixed-bed unit at liquid-phase conditions as follows:

| | |
|---|---|
| Pressure | 500 psig |
| Avg. Temperature | 385-450° F. |
| Benzene: C$_2$= Mole Ratio | 10:1 |
| C$_2$=, WHSV | 0.6 |

Note: C$_2$= stands for ethylene

In this Example, an extrudate MCM-22 catalyst containing 65 wt % zeolite and 35 wt % alumina was evaluated according to the above conditions. The total liquid products were obtained with time on stream and analyzed on GC. The results are shown in Table 5.

TABLE 5

Performance of MCM-22 for EB Synthesis

| Max T, °F. | Avg T, °F. | HOS | C$_2$= Conv | Product Selectivity | | |
|---|---|---|---|---|---|---|
| | | | | EB/B | DEB/B | C$_9$+/EB |
| 412 | 388 | 2 | 98.3 | 0.148 | 0.064 | 0.082 |
| 414 | 389 | 45 | 99.6 | 0.151 | 0.067 | 0.070 |
| 457 | 435 | 200 | 99.6 | 0.157 | 0.068 | 0.072 |

Note: B = Benzene; EB = Ethylbenzene; DEB = Di-ethylbenzene

EXAMPLE 2

This Example illustrates the benefit of treating the MCM-22 catalyst with water for EB performance The MCM-22 catalyst used in Example 1 was saturated with distilled water at room temperature and pressure before EB evaluation For example, 20 g of MCM-22 catalyst required about 16.3 g of water to reach its saturation point. The hydrated catalyst was then loaded into the reactor and evaluated for EB performance. The results are shown in Table 6.

TABLE 6

Performance of Hydrated MCM-22 for EB Synthesis

| Max T, °F. | Avg T, °F. | HOS | C$_2$= Conv | Product Selectivity | | |
|---|---|---|---|---|---|---|
| | | | | EB/B | DEB/B | C$_9$+/EB |
| 431 | 411 | 7 | 99.1 | 0.171 | 0.047 | 0.066 |
| 455 | 420 | 18 | 99.7 | 0.176 | 0.040 | 0.041 |

The comparison of Tables 5 and 6 shows that treating MCM-22 catalyst with water increases significantly its selectivity for EB production by reducing the yield of DEB and C$_9$+by-products. The reduction in multialkylated benzene production translates into the economic advantage by decreasing a recycle stream to the reactor for dealkylation reactions.

What is claimed is:

1. A process for preparing an alkylbenzene, said process comprising contacting an olefin having from 2 to 6 carbon atoms and liquid benzene with a catalyst under sufficient alkylation conditions, said catalyst comprising a hydrated synthetic porous crystalline material characterized by an X-ray diffraction pattern including valves substantially as set forth in Table 1 of the specification, said hydrated crystalline material comprising at least 10% by weight of liquid water included in the pore space of the crystalline material when the crystalline material is first contacted with said benzene and olefin, wherein the alkylation conditions include a combination of temperature and pressure sufficient to maintain said benzene and said water in the liquid state, wherein said hydrated crystalline material is hydrated by placing the crystalline material in liquid water for a time sufficient to sorb at least 10% by weight of water in the pore space of the crystalline material.

2. A process according to claim 1, wherein said crystalline material is saturated with liquid water when the crystalline material is first contacted with said benzene and olefin.

3. A process according to claim 1, wherein the synthetic porous crystalline material is characterized by an X-ray diffraction pattern including values substantially as set forth in Table 2 of the specification.

4. A process according to claim 1, wherein the synthetic porous crystalline material is characterized by an X-ray diffraction pattern including values substantially as set forth in Table 3 of the specification.

5. A process according to claim 1, wherein the synthetic porous crystalline material is characterized by an X-ray diffraction pattern including values substantially as set forth in Table 4 of the specification.

6. A process according to claim 1, wherein the synthetic porous crystalline material has a composition comprising the molar relationship $$X_2O_3:(n)YO_2,$$

wherein n is at least about 10, X is a trivalent element and Y is a tetravalent element.

7. A process according to claim 1, wherein the synthetic porous crystalline material is in the hydrogen form.

8. A process according to claim 1, wherein the catalyst comprises a binder selected from alumina, silica or silica-alumina.

9. A process according to claim 1 in which the alkylation is carried out at a pressure from 400 to 800 psig and at a temperature from 300° to 600° F.

10. A process according to claim 1 in which the alkylation is carried out at a temperature from 200° to 500° F.

11. A process according to claim 1 in which the alkylation is carried out at a temperature from 300° to 500° F.

12. A process according to claim 1, wherein said olefin is ethylene.

13. A process according to claim 2, wherein said olefin is ethylene.

* * * * *